United States Patent
Bonde et al.

(10) Patent No.: US 10,086,191 B2
(45) Date of Patent: Oct. 2, 2018

(54) MEDICAL LEADS HAVING A DISTAL BODY AND AN OPENLY COILED FILAR

(71) Applicant: Medtronic, Inc., Minneapolis, MN (US)

(72) Inventors: Eric H. Bonde, Minnetonka, MN (US); Phillip C. Falkner, Minneapolis, MN (US); Michael T. Hegland, Mounds View, MN (US); Brian T. Stolz, Bloomington, MN (US); Patrick D. Wells, Minneapolis, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 223 days.

(21) Appl. No.: 14/395,247

(22) PCT Filed: Jan. 29, 2013

(86) PCT No.: PCT/US2013/023626
§ 371 (c)(1),
(2) Date: Oct. 17, 2014

(87) PCT Pub. No.: WO2013/158188
PCT Pub. Date: Oct. 24, 2013

(65) Prior Publication Data
US 2015/0133955 A1 May 14, 2015

Related U.S. Application Data

(60) Provisional application No. 61/635,798, filed on Apr. 19, 2012.

(51) Int. Cl.
*A61N 1/05* (2006.01)
*A61B 17/34* (2006.01)

(52) U.S. Cl.
CPC .............. *A61N 1/05* (2013.01); *A61B 17/3468* (2013.01); *A61N 1/0558* (2013.01)

(58) Field of Classification Search
CPC ........ A61N 1/05; A61N 1/057; A61N 1/0573; A61B 17/3468
See application file for complete search history.

(56) References Cited

U.S. PATENT DOCUMENTS 4,506,679 A * 3/1985 Mann ..................... A61N 1/057
607/126
4,945,922 A * 8/1990 van Krieken .......... A61N 1/057
607/126

(Continued)

FOREIGN PATENT DOCUMENTS

EP 0972538 1/2000

OTHER PUBLICATIONS

PCT/US2013/023626 Written Opinion of the International Search Report dated Aug. 13, 2013.

(Continued)

*Primary Examiner* — Sarah W Aleman
(74) *Attorney, Agent, or Firm* — Withers & Keys, LLC (57) ABSTRACT

Medical leads have one or more openly coiled filars and a distal body coupled to the openly coiled filars. The openly coiled filars provide a lead with compliance and elasticity while the distal body provides the firmness needed for placement and support of the electrodes. The openly coiled filars may transition to a linear distal portion that extends to the distal body, and the distal body may have proximal tines that fold proximally to become adjacent to the linear distal portion of the filars. The openly coiled filars may instead extend to the distal body and the proximal tines may be laterally arced to then fold against the lateral surface of the coiled filars. The tines may fold distally during explantation to allow the distal body to release and exit the body.

20 Claims, 8 Drawing Sheets (56) References Cited

U.S. PATENT DOCUMENTS

| | | |
|---|---|---|
| 5,571,157 A | 11/1996 | McConnell |
| 6,240,322 B1 | 5/2001 | Peterfeso et al. |
| 8,036,756 B2 | 10/2011 | Swoyer et al. |
| 2006/0015164 A1 | 1/2006 | Partridge et al. |
| 2007/0255366 A1 | 11/2007 | Gerber et al. |
| 2007/0255368 A1 | 11/2007 | Bonde et al. |
| 2007/0255369 A1* | 11/2007 | Bonde .................. A61N 1/0551 607/116 |
| 2008/0183257 A1* | 7/2008 | Imran .................. A61N 1/0558 607/117 |
| 2010/0094364 A1 | 4/2010 | McDonald |
| 2010/0268310 A1 | 10/2010 | Bonde et al. |
| 2011/0071608 A1 | 3/2011 | Fleischhacker et al. |
| 2012/0071958 A1* | 3/2012 | Klardie ................ A61N 1/0551 607/148 |

OTHER PUBLICATIONS

PCT/US2013/023626 International Search Report dated Dec. 10, 2013.
EP-13703969 Communication dated Oct. 31, 2017.

\* cited by examiner

MEDICAL LEADS HAVING A DISTAL BODY AND AN OPENLY COILED FILAR

TECHNICAL FIELD

Embodiments are related to medical leads that carry stimulation signals. More particularly, embodiments are related to medical leads that have a distal body and openly coiled filars.

BACKGROUND

Medical leads are used in conjunction with a medical device that generates stimulation signals to deliver the stimulation signals from the medical device to a target stimulation site within a body of a patient. The medical leads may be implanted through a percutaneous procedure where an introducer needle is inserted into the body, and a medical lead is inserted through a lumen in the needle. A stylet may be included within a lumen of the medical lead to guide the medical lead from the needle to the target site.

One issue when implanting the medical lead is that the needle must be of adequate size to facilitate the introduction of the medical lead. However, a smaller needle is less bothersome to the patient. Thus, minimizing the diameter of the lead is desirable so that the size of the introducer needle may also be minimized.

Another issue that occurs once the medical lead is implanted is that the medical lead needs to have a fixed position at the target site, which is particularly true when assessing the efficacy of therapy during a trial period. Movements by the patient may encourage the medical lead to migrate and therefore a fixation structure may be required to provide the fixation of the lead at the target site. However, the structure for fixation may contribute to the size of the medical lead which may call for an undesirable increase in the size of the introducer needle. Furthermore, explantation of the lead may be more difficult due to the presence of the fixation structure which resists movement in the direction of explantation.

The effectiveness of a fixation structure may also be limited by the compliance of the body of the lead. The body of the lead needs a degree of firmness to support the electrodes and to maintain their alignment when at the target site. Yet a stiff lead body extending toward the proximal end of the lead is counterproductive to the fixation structure.

SUMMARY

Embodiments address issues such as these and others by providing a body that utilizes one or more openly coiled filars that act as a portion of the lead body and provides a relatively high degree of compliance. A distal body is present at the distal end of the coiled filar where the distal body provides a firmer support for the electrodes. The distal body may include tines on the proximal end that offer fixation. The coiled filar may have a linear region proximal of the distal body, and the tines may collapse in the proximal direction to avoid increasing the diameter of the lead. Furthermore, the tines may collapse in the opposite direction when subject to a removal force during explantation.

Embodiments provide a medical lead that includes a filar with an openly coiled center portion. The medical lead further includes a distal body having an electrode, with a distal portion of the filar passing through the distal body and being coupled to the electrode.

Embodiments further provide a medical lead that includes an openly coiled filar that has a linear distal end. The medical lead includes a distal body having an electrode and also having at least one tine on a proximal end, with a distal portion of the linear distal end of the coiled filar passing through the distal body and being coupled to the electrode. A junction of the at least one tine to the distal body provides a hinge point, the at least one tine being rotatable about the hinge point between a collapsed state and an extended state. The at least one tine rotates in the proximal direction from the extended state to the collapsed state to become adjacent to the linear distal end of the coiled filar.

Embodiments provide a medical system that includes a stimulation device and a medical lead with a proximal end coupled to the stimulation device. The medical lead includes an openly coiled filar that has a proximal end coupled to the stimulation device and has a linear distal end. The medical lead further includes a distal body having an electrode and also having at least one tine on a proximal end, with a distal portion of the linear distal end of the coiled filar passing through the distal body and being coupled to the electrode. A junction of the at least one tine to the distal body provides a hinge point, the at least one tine being rotatable about the hinge point between a collapsed state and an extended state. The at least one tine rotates in the proximal direction from the extended state to the collapsed state to become adjacent to the linear distal end of the coiled filar.

Embodiments provide a method of positioning a medical lead that involves providing the medical lead having an openly coiled filar that has a linear distal end. The medical lead also has a distal body having an electrode and also having at least one tine on a proximal end, with a distal portion of the linear distal end of the coiled filar passing through the distal body and being coupled to the electrode. A junction of the at least one tine to the distal body provides a hinge point, the at least one tine being rotatable about the hinge point between a collapsed state and an extended state. The at least one tine rotates in the proximal direction from the extended state to the collapsed state to become adjacent to the linear distal end of the coiled filar. The method further involves implanting the medical lead by routing the medical lead through a needle with the at least one tine in the collapsed state and with the at least one tine achieving the extended state upon exiting the needle. The method also involves explanting the medical lead by removing the lead in the proximal direction, wherein during explanting the at least one tine rotates distally from the extended state to a second collapsed state where the at least one tine is adjacent to the distal body.

DETAILED DESCRIPTION

Embodiments of medical leads include a compliant lead body formed by one or more openly coiled filars with a firmer distal body coupled to distal ends of the one or more filars. The distal body supports the electrodes, and some embodiments of the distal body may include proximal tines that collapse in the proximal direction to minimize the distal body diameter. Furthermore, in some embodiments the tines may collapse in the distal direction when the lead receives a removal force during explantation.

Figure 1:
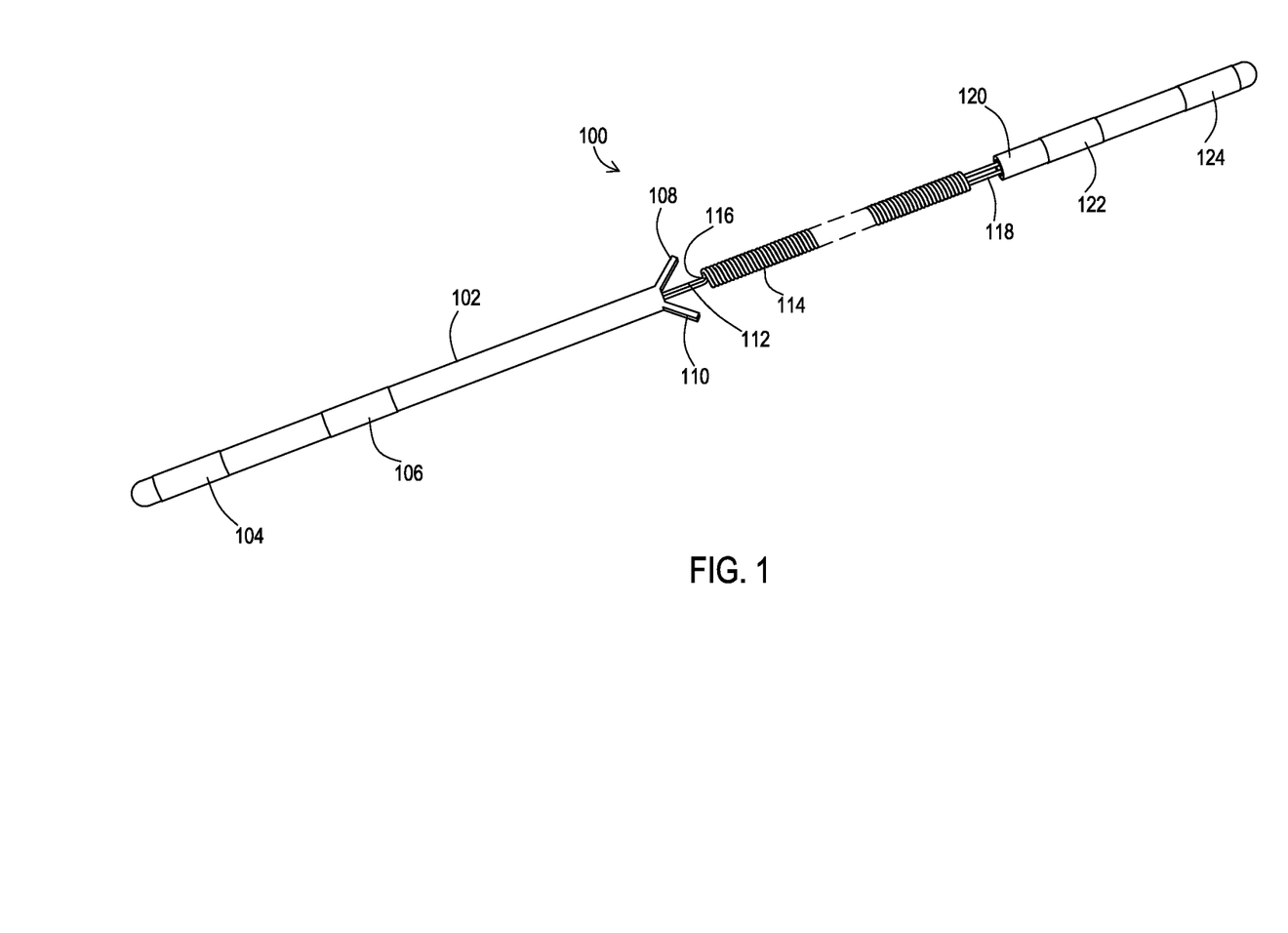
FIG. 1 shows an example of a medical lead according to various embodiments.
Figure 2:
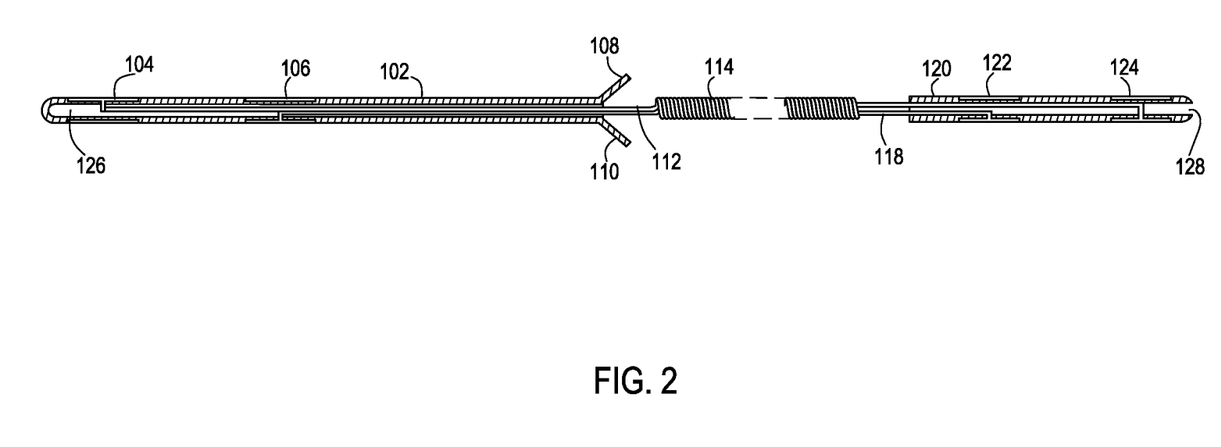
FIG. 2 shows a longitudinal cross-section of the medical lead of FIG. 1.

FIGS. 1 and 2 show one example of a medical lead 100 having a central portion 114 of a filar that is openly coiled. In other words, the coiled filar is not surrounded by a protective tubular jacket but is instead itself the lead body. This openly coiled filar portion 114 provides a relatively high degree of compliance and elasticity for the lead 100. The filar may be constructed of various biocompatible conductors such as stainless steel alloys (316L, 316LVM, MP35N, etc.) or other biocompatible metals and alloys such as alloys of platinum (Pt—Ir) or alloys of titanium (TiOsteum®, Ti-15Mo) that have a non-conductive coating such as polyethylene-co-tetrafluoroethylene (ETFE), polytetrafluoroethylene (PTFE or Teflon®), polyurethanes, polyimides, etc. The coiled shape defines a lumen 116 through which a stylet may be passed when implanting the medical lead 100.

In this particular example, both a proximal filar portion 118 and a distal filar portion 112 are linear rather than coiled. These linear portions 112, 118 enter into respective distal and proximal bodies 102, 120. It will be appreciated that in other examples, one or both of these portions may be coiled as well, as in the example discussed below in relation to FIGS. 7 and 8.

The proximal body 120 of FIGS. 1 and 2 provides a firmer support for one or more contacts 122, 124 that are ultimately connected to a stimulation device. The proximal body 120 may be inserted into a bore within a stimulation device where the electrical connections occur. The proximal body 120 may be constructed of various nonconductive biocompatible materials such as polyurethane, polyether block amide (PEBA or PEBAX®), polyether ether ketone or polyaryletherketone (PEEK) and others. The proximal body 120 may define a lumen 128 that allows a stylet to be inserted during implantation of the medical lead 100.

The proximal portion 118 of the filar(s) may extend through the proximal body 120 until reaching the respective contacts 122, 124, The proximal portion 118 of the filar(s) is then physically and electrically coupled to the respective contacts 122, 124.

The distal body 102 provides a firmer support for one or more electrodes 104, 106 that are ultimately positioned at the target stimulation site within the body of the patient. The distal body 102 may be constructed of various nonconductive biocompatible materials such as polyurethane, silicone, and surface-modified endgroup (SME) polyurethanes to provide such firmness. The distal body 102 may define a lumen 126 that allows a stylet to be inserted when implanting the medical lead 100.

The distal portion 112 of the filar(s) may extend through the distal body 102 until then coupling to the respective electrode 104, 106. The filar may be present within the lumen 126 or may otherwise tunnel through the distal body 102 until reaching the electrode 104, 106. Furthermore, the distal-most region of the distal filar portion 112 which is present within the lumen 126 may be coiled rather than linear, which provides an additional mechanical advantage during explantation to minimize strain on the bond of the filar portions 112 to the electrodes 104, 106. Another manner of minimizing such strain during explantation involves using a polyurethane coating directly on the metal of the filar portions 112 and then allowing the polyurethane coating to achieve a bond with the polymer forming the distal body 102.

To provide fixation for the electrodes 104, 106, the distal body 102 may further define one or more proximal tines 108, 110. As shown in FIGS. 1 and 2, two tines 108, 110 are present on opposite sides of the proximal end of the distal body 102 but any number of tines may be present in various embodiments. These tines have a natural extended state as shown in FIGS. 1 and 2 whereby the tines 108, 110 extend from the distal body 102 at a particular angle. In this extended state, the tines 108, 110 effectively catch upon the surrounding tissue of the body to resist movement in the proximal and distal directions. The amount of fixation force created by the tines 108, 110 can be controlled by the physical dimensions chosen for the tines 108, 110 including the angle, the length, the width, the thickness, and the geometry. Thus, the medical lead 100 may be selected for a particular implantation scenario based on having a tine design that meets the fixation requirements of the scenario.

The distal body 102 and tines 108, 110 may be constructed by being molded onto the linear distal end 112 of the filars. An alternative construction would be to use tine and tubing components assembled manually and bonding them together with adhesives or thermally reflowing the polymers together.

During implantation, the tines 108, 110 can be forced into a collapsed state where the tines 108, 110 are rotated proximally about a hinge point that occurs at the junction of the tines 108, 110 to the distal body 102 by insertion in the distal direction into a lumen of an introducer needle. Once fully rotated, the tines 108, 110 become adjacent to the linear distal portion 112 of the filar(s) so that the overall diameter of the medical lead is no greater than the diameter of the distal body 102. Therefore, the presence of the tines 108, 110 does not require an increase in size of the lumen of the introducer needle.

During explantation, the tines 108, 110 can be forced into a collapsed state where the tines 108, 110 are rotated distally to become adjacent to the distal body 102. The extraction force applied to the medical lead 102 is greater than the migration forces that the medical lead 102 is subject to such that the extraction force overcomes the natural reluctance of the tines 108, 110 to rotate distally from the extended state to this collapsed state.

Figure 3:
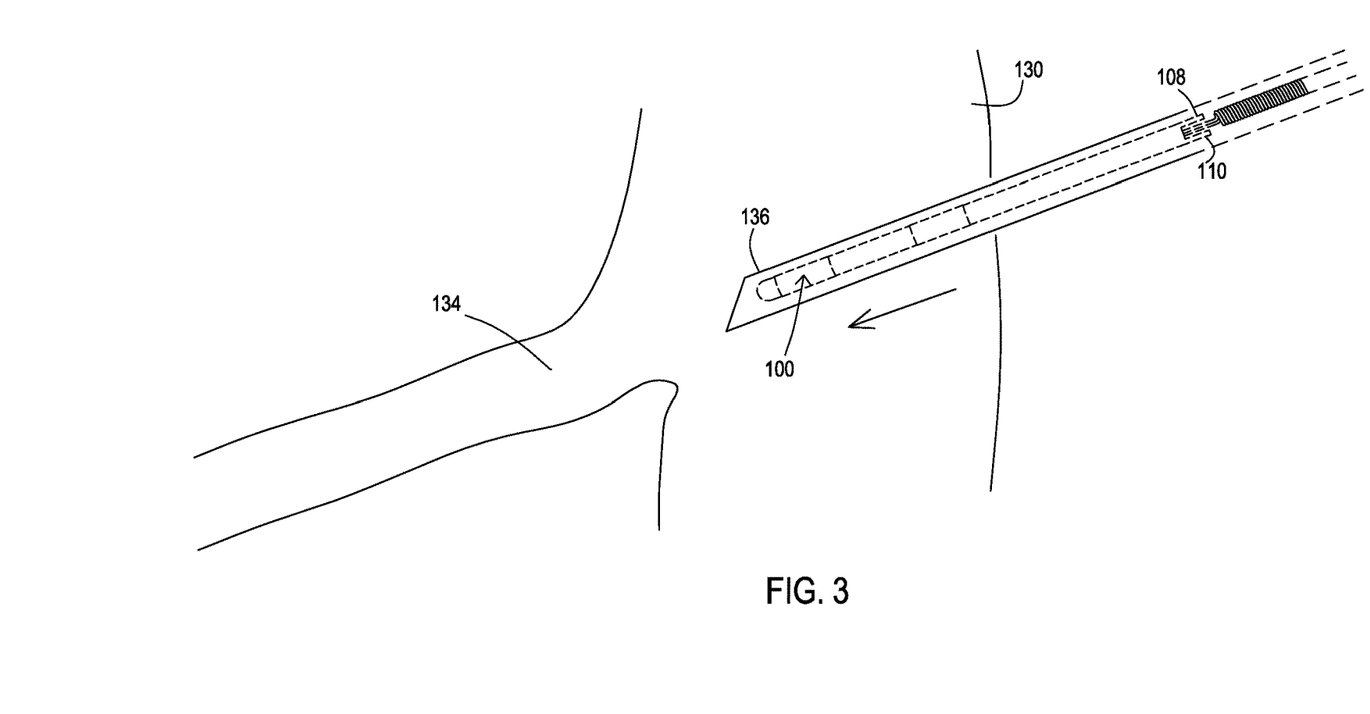
FIG. 3 shows a first stage of one example of an implantation procedure of the medical lead of FIG. 1.
Figure 4:
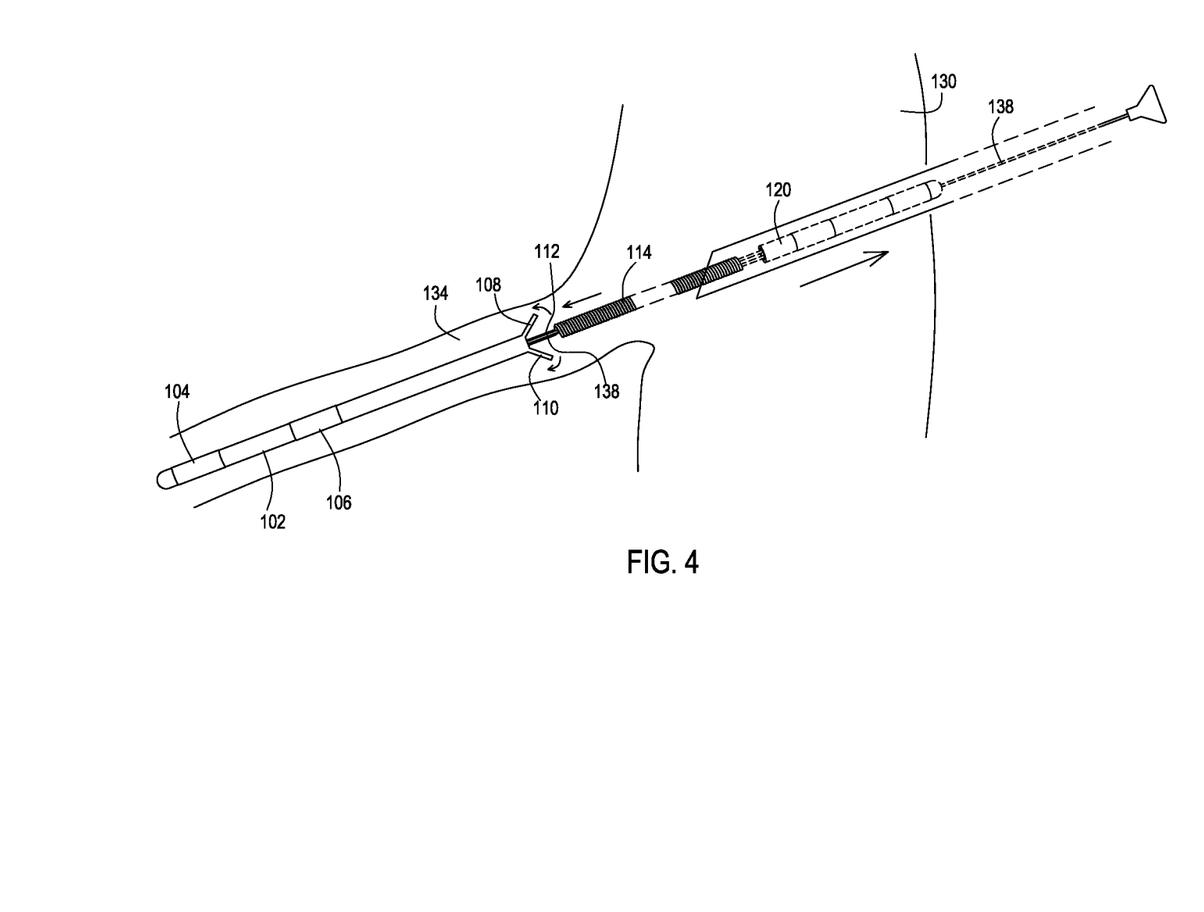
FIG. 4 shows a second stage of the implantation procedure.

One example of the process of implantation is shown in FIGS. 3 and 4. In FIG. 3, the medical lead of FIG. 1 is located within a lumen of the introducer needle 136, and the titres 108, 110 are in the proximally collapsed state. The introducer needle 136 is inserted through the body 130 of the patient and directed toward a target stimulation site. In this particular example, the target stimulation site is in close proximity to the sacrum in order to stimulate nearby the sacral nerve. For instance, the electrodes 104, 106 may be positioned within a foramen 134 of the sacrum such that the needle 136 is directed to the foramen 134.

In this particular example, one the needle 136 has aligned with the foramen 134, the medical lead 100 is advanced distally from the needle 136 and through the foramen 134 by manipulation of a stylet 138 that is present within the lumens 116, 126, and 128 of the medical lead 100. The stylet 138 is used to steer the distal body 102 to the desired location relative to the sacral nerve.

As shown in FIG. 4, upon the distal body 102 exiting the needle 136, the tines 108, 110 naturally begin to rotate distally to the extended state. However, forward motion of the lead 100 by an insertion force from the stylet 138 overcomes any retention force being created by the tines 108, 110. Upon reaching the target site, the needle 136 and style 138 are then removed.

Figure 5:
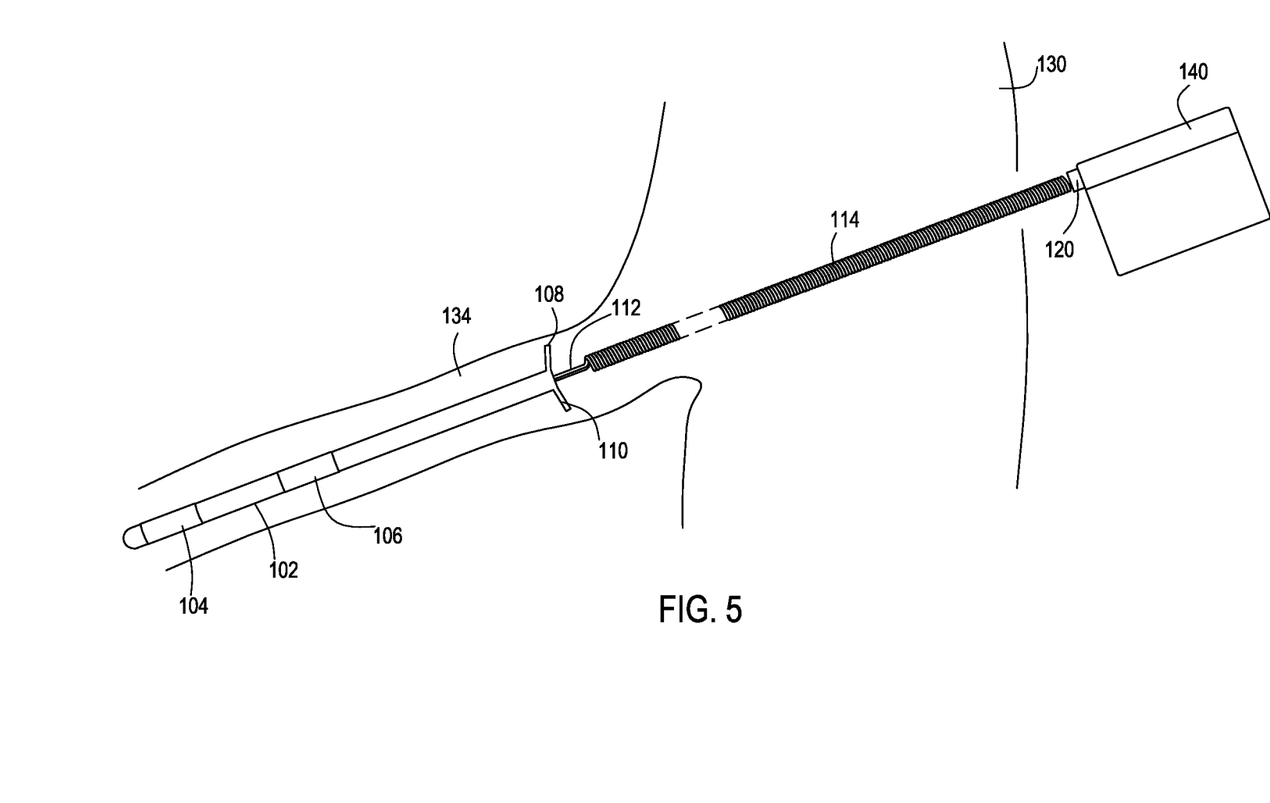
FIG. 5 shows the medical lead once implanted and connected to a stimulation device.

FIG. 5 shows the medical lead 100 with the distal body 102 in the target site with the electrodes 104, 106 being in proximity to the sacral nerve. The tines 108, 110 are in their fully extended state and provide maximum resistance to further movements of the distal body 102. The openly coiled filar portion 114 extends proximally back to a location where a stimulation device 140 is being positioned with the proximal body 120 being coupled to the stimulation device 140. In this example, the stimulation device 140 is a trial stimulation device being positioned externally on the body 130 such that the filar portion 114 extends beyond the outer surface of the body 130. However, it will be appreciated that in other examples the stimulation device 140 may be implanted within a pocket formed within the body 130.

Figure 6:
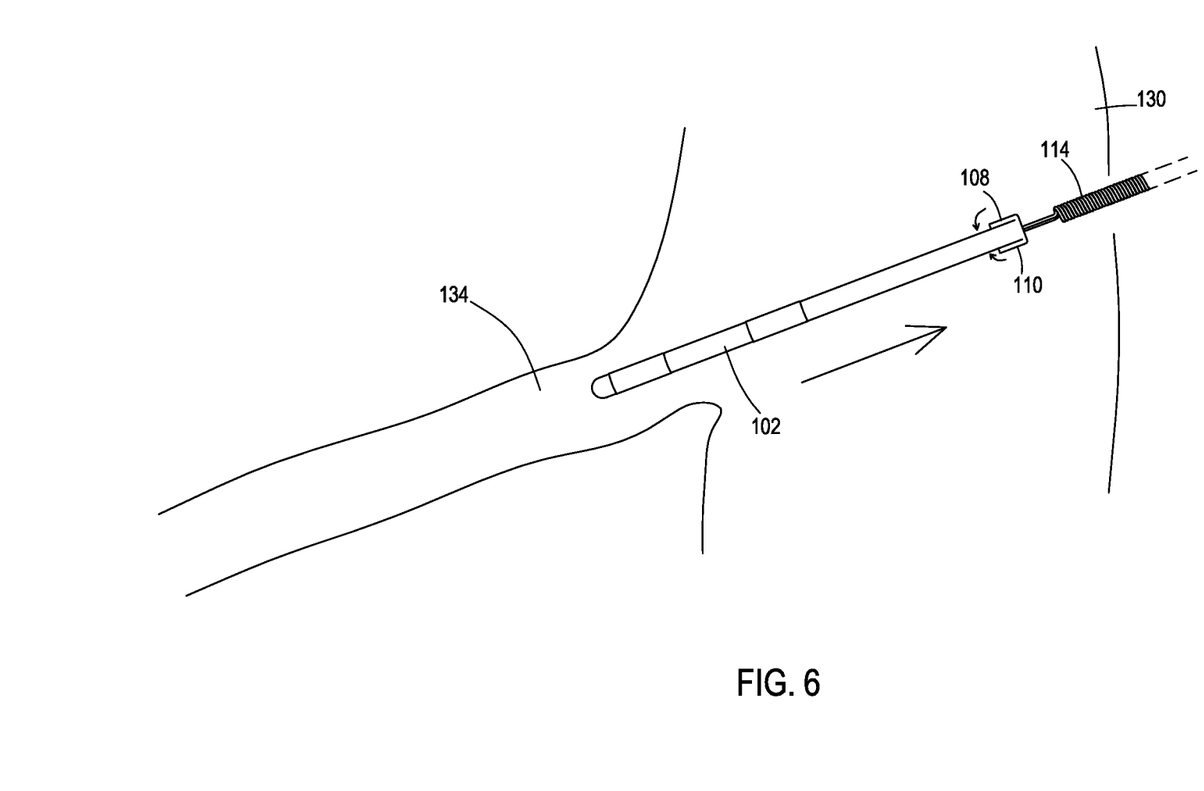
FIG. 6 shows an example of an explantation of the medical lead.

It may be desirable to subsequently explant the medical lead 100. This is particularly the case where the medical lead 100 has been implanted for a stimulation trial. This explantation of the medical lead 100 is shown in FIG. 6. In this case, a removal force is applied in the proximal direction to the proximal body 120 and the proximal end of the filar portion 114. This proximal force causes proximal movement of the distal body 102 which causes the tines 108, 110 to rotate distally until achieving the distally collapsed state as shown. The distal body 102 then proceeds proximally until exiting the body 130.

Figure 7:
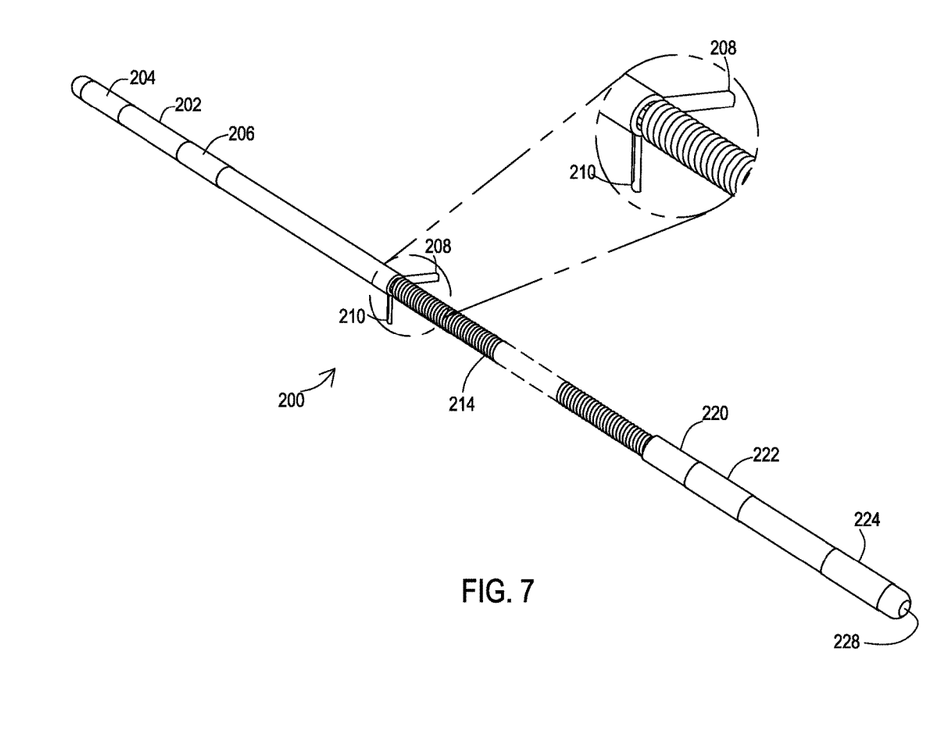
FIG. 7 shows another example of a medical lead according to various embodiments.
Figure 8:
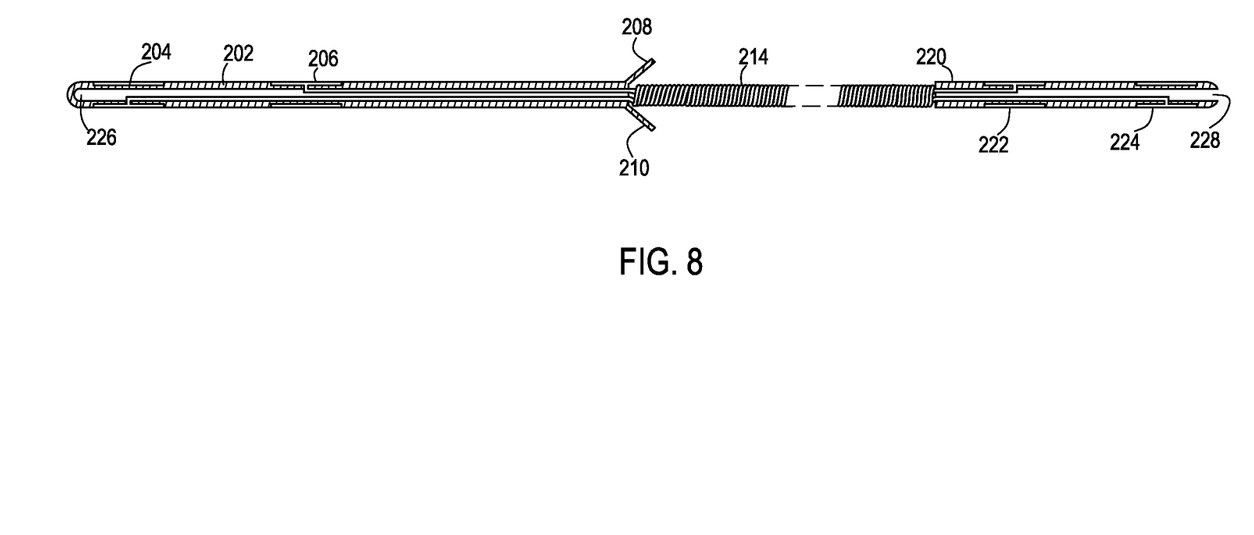
FIG. 8 shows a longitudinal cross-section of the medical lead of FIG. 7.

FIGS. 7 and 8 show another example of a medical lead 200 having a central portion 214 of a filar that is openly coiled. Like the prior example, this openly coiled filar portion 214 provides a relatively high degree of compliance for the lead 200. The filar may be constructed of the same various biocompatible conductors with a non-conductive coating as the previous example. The coiled shape defines a lumen through which the stylet may be passed when implanting the medical lead 200. In this particular example, the filar portion 214 extends from a proximal body 220 to a distal body 202.

The proximal body 220 provides a firmer support for one or more contacts 222, 224 that are ultimately connected to the stimulation device. The proximal body 220 may be inserted into a bore within the stimulation device where the electrical connections occur. The proximal body 220 may be constructed of the same various nonconductive biocompatible materials as the previous example. The proximal body 220 may define a lumen 228 that allows the stylet to be inserted during implantation of the medical lead 200.

The filar(s) may extend through the proximal body 220 until reaching the respective contacts 222, 224. The filar(s) then physically and electrically coupled to the respective contacts 222, 224.

The distal body 202 provides a firmer support for one or more electrodes 204, 206 that are ultimately positioned at the target stimulation site within the body of the patient. The distal body 202 may be constructed of the same various nonconductive biocompatible materials such as the previous example to provide such firmness. The distal body 202 may define a lumen 226 that allows a stylet to be inserted when implanting the medical lead 200.

The filar(s) may extend through the distal body 202 until then coupling to the respective electrode 204, 206. The filar may be present within the lumen 226 or may otherwise tunnel through the distal body 202 until reaching the electrode 204, 206. Furthermore, the distal-most region of the filars which is present within the lumen 226 may be coiled rather than linear, which provides an additional mechanical advantage during explantation to minimize strain on the bond of the filars to the electrodes 204, 206. Another manner of minimizing such strain during explantation involves using a polyurethane coating directly on the metal of the filars and then allowing the polyurethane coating to achieve a bond with the polymer forming the distal body 202.

To provide fixation for the electrodes 204, 206, the distal body 202 may further define one or more proximal tines 208, 210. As shown in FIGS. 7 and 8, two tines 208, 210 are present on opposite sides of the proximal end of the distal body 202 but any number of tines may be present in various embodiments. These tines 208, 210 have a natural extended state as shown in FIGS. 7 and 8 whereby the tines 208, 210 extend from the distal body 202 at a particular angle. In this extended state, the tines 208, 210 effectively catch upon the surrounding tissue of the body to resist movement in the axial proximal and distal directions.

The distal body 202 and tines 208, 210 may be constructed in the same manner as discussed above for the embodiment of FIG. 1 For instance, the distal body 202 and tines 208, 210 may be molded onto the linear distal end 112 of the filars. An alternative construction would again be to use separate components (tines, tubings, etc.) assembled manually and bonding them together with adhesives or thermally re-flowing the polymers together.

During implantation, the tines 208, 210 can be forced into a collapsed state where the tines 208, 210 are rotated proximally about a hinge point that occurs at the junction of the tines 208, 210 to the distal body 202 by insertion in the distal direction into a lumen of the introducer needle. Once fully rotated, the tines 208, 210 become adjacent to the central portion 214 of the filar(s). The tines 208, 210 define an arced shape in a lateral dimension that rests on the arced lateral surface of the central portion 214. Thus, when the overall diameter of the medical lead 200 is no greater than the diameter of the distal body 202 and where the diameter of the central portion 214 is slightly smaller than that of the distal body 202, the presence of the tines 208, 210 does not require an increase in size of the lumen of the introducer needle.

During explantation, the tines 208, 210 can be forced into a collapsed state where the tines 208, 210 are rotated distally to become adjacent to the distal body 202. The extraction force applied to the medical lead 202 is greater than the migration forces that the medical lead 200 is subject to such that the extraction force overcomes the natural reluctance of the tines 208, 210 to rotate distally from the extended state to this collapsed state.

The implantation of the medical lead 200 proceeds in the same manner discussed above in relation to FIGS. 3 and 4. Likewise, the explantation of the medical lead 200 proceeds in the same manner discussed above in relation to FIG. 6.

While embodiments have been particularly shown and described, it will be understood by those skilled in the art that various other changes in the form and details may be made therein without departing from the spirit and scope of the invention.

What is claimed is:
1. A medical lead, comprising:
a filar with an openly coiled central portion, the filar including a linear distal end including a proximal portion and a distal portion;

a distal body having an electrode, with the distal portion of the linear distal end passing through the distal body and being directly coupled to the electrode and with the proximal portion of the linear distal end being outside of the distal body; and at least one tine extending from a most proximal point of the distal body, the at least one tine extending proximally over a portion of the filar that is not within the distal body such that an outermost surface of the tine immediately adjacent the most proximal point of the distal body and an outermost surface of the distal body at the most proximal point of the distal body are at a same radial distance from a centerline passing through the distal body.

2. The medical lead of claim 1, further comprising a proximal body separated from the distal body and having a contact, with a proximal end of the coiled filar passing through the proximal body and being coupled to the contact.

3. The medical lead of claim 1, wherein the distal body is molded onto the distal portion of the linear distal end of the coiled filar.

4. The medical lead of claim 1, wherein the openly coiled filar is a first openly coiled filar, the medical lead further comprising a second openly coiled filar paired with the first openly coiled filar, the second openly coiled filar having a linear distal end and wherein the distal body has a second electrode that is coupled to the linear distal end of the second openly coiled filar.

5. The medical lead of claim 1, wherein a junction of the at least one tine to the distal body provides a hinge point, the at least one tine being rotatable about the hinge point between a collapsed state and an extended state, the at least one tine rotating in the proximal direction from the extended state to the collapsed state to become adjacent to the linear distal end of the coiled filar.

6. The medical lead of claim 5, wherein the distal portion has a first and a second tine.

7. The medical lead of claim 1, wherein the distal body has at least one tine on a proximal end with the at least one tine having an arced shape in a lateral dimension, a junction of the at least one tine to the distal body providing a hinge point, the at least one tine being rotatable about the hinge point between a collapsed state and an extended state, the at least one tine rotating in the proximal direction from the extended state to the collapsed state to become adjacent to the coiled filar.

8. A medical lead, comprising:
an openly coiled filar that has a linear distal end including a proximal portion and a distal portion;
a distal body having an electrode and also having at least one tine on a proximal end, with the distal portion of the linear distal end of the coiled filar passing through the distal body and being directly coupled to the electrode and with the proximal portion of the linear distal end being outside of the distal body, a junction of the at least one tine to the distal body providing a hinge point, the at least one tine being rotatable about the hinge point between a collapsed state and an extended state, the at least one tine rotating in the proximal direction from the extended state to the collapsed state to become adjacent to the proximal portion of the linear distal end of the coiled filar.

9. The medical lead of claim 8, further comprising a proximal body separated from the distal body and having a contact, with a proximal end of the coiled filar passing through the proximal body and being coupled to the contact.

10. The medical lead of claim 8, wherein the distal body is molded onto the distal portion of the linear distal end of the coiled filar.

11. The medical lead of claim 8, wherein the openly coiled filar is a first openly coiled filer, the medical lead further comprising a second openly coiled filar paired with the first openly coiled filar, the second openly coiled filar having a linear distal end and wherein the distal body has a second electrode that is coupled to the linear distal end of the second openly coiled filar.

12. The medical lead of claim 8, wherein the distal portion has a first and a second tine.

13. The medical lead of claim 12, wherein the first tine and the second tine are positioned on opposite sides of the distal body.

14. A medical system, comprising:
a stimulation device; and
a medical lead with a proximal end coupled to the stimulation device, the medical lead comprising:
an openly coiled filar that has a proximal end coupled to the stimulation device and has a linear distal end including a proximal portion and a distal portion; and
a distal body having an electrode and also having at least one tine on a proximal end, with the distal portion of the linear distal end of the coiled filar passing through the distal body and being directly coupled to the electrode and with the proximal portion of the linear distal end being outside of the distal body, a junction of the at least one tine to the distal body providing a hinge point, the at least one tine being rotatable about the hinge point between a collapsed state and an extended state, the at least one tine rotating in the proximal direction from the extended state to the collapsed state to become adjacent to the proximal portion of the linear distal end of the coiled filar.

15. The medical system of claim 14, wherein the medical lead further comprises a proximal body separated from the distal body and having a contact, with a proximal end of the coiled filar passing through the proximal body and being coupled to the contact.

16. The medical system of claim 14, wherein the distal body is molded onto the distal portion of the linear distal end of the coiled filar.

17. The medical system of claim 14, wherein the openly coiled filar is a first openly coiled filer and the medical lead further comprises a second openly coiled filar paired with the first openly coiled filar, the second openly coiled filar having a linear distal end and wherein the distal body has a second electrode that is coupled to the linear distal end of the second openly coiled filar.

18. The medical system of claim 14, wherein the distal portion has a first and a second tine.

19. The medical system of claim 18, wherein the first tine and the second tine are positioned on opposite sides of the distal body.

20. A method of positioning a medical lead, comprising:
providing the medical lead having an openly coiled filar that has a linear distal end including a proximal portion and a distal portion, the medical lead also having a distal body having an electrode and also having at least one tine on a proximal end, with the distal portion of the linear distal end of the coiled filar passing through the distal body and being directly coupled to the electrode and with the proximal portion of the linear distal end being outside of the distal body, a junction point of the at least one tine to the distal body providing a hinge point, the at least one tine being rotatable about the hinge point between a collapsed state and an extended state, the at least one tine rotating in the proximal direction from the extended state to the collapsed state to become adjacent to the proximal portion of the linear distal end of the coiled filar;

implanting the medical lead by routing the medical lead through a needle with the at least one tine in the collapsed state with the at least one tine achieving the extended state upon exiting the needle; and explanting the medical lead by removing the lead in the proximal direction, wherein during explanting the at least one tine rotates distally from the extended state to a second collapsed state where the at least one tine is adjacent to the distal body.

\* \* \* \* \*